United States Patent [19]

Weber

[11] Patent Number: 5,405,837
[45] Date of Patent: Apr. 11, 1995

[54] METHOD FOR THE TREATMENT OF NEOPLASTIC DISEASE UTILIZING TIAZOFURIN AND RIBAVIRIN

[75] Inventor: George Weber, Indianapolis, Ind

[73] Assignee: Indiana University Foundation, Bloomington, Ind.

[21] Appl. No.: 65,348

[22] Filed: May 18, 1993

[51] Int. Cl.⁶ .............................................. A61K 31/70
[52] U.S. Cl. ...................................................... 514/43
[58] Field of Search ...................... 514/23, 42, 43, 908, 514/922

[56] References Cited

U.S. PATENT DOCUMENTS 4,211,771  7/1980  Witkowski .......................... 536/28.8
4,680,285  7/1987  Robins ................................... 514/23

OTHER PUBLICATIONS

Zhen et al., Cancer Investigation, vol. 10, No. 6, pp. 505-511, (1992).
Look et al., Gynecologic Oncology, vol. 47, pp. 66-70, (1992).
Ban et al., Biochemical and Biophysical Research Communications, vol. 184, No. 2, pp. 551-559, (1992).
Weber et al., Cancer Research, vol. 53, pp. 5982-5986, (1993).
Jayaram et al., Cancer Chemotherapy and Pharmacology, pp. 93-96, (1992).
Jayaram et al., Int. J. Cancer, vol. 51, pp. 182-188, (1992).
Batist et al., Investigational New Drugs, vol. 3, pp. 349-355 (1985).
Roberts et al., Cancer Treatment Reports, vol. 71, No. 2, pp. 141-149, (1987).
Kovacs et al., J. Med. Chem, vol. 25, No. 1, pp. 107-108, (1982).
Taniki et al., Cancer Biochem. Biophys., vol. 13, pp. 295-302, (1993).
Tricot et al., Int. J. of Cell Cloning, vol. 8, pp. 161-170, (1990).
Tricot et al., Cancer Research, vol. 47, pp. 4988-4991, (1987).
Tricot et al., Cancer Research, vol. 49, pp. 3696-3701, (1989).
Weber et al., Cancer Communications, vol. 3, No. 3, pp. 61-66, (1991).
Weber et al., Advances in Enzyme Regulation, vol. 27, pp. 405-433, (1988).
Weber, Advances In Enzyme Regulation, vol. 29, pp. 75-95.
Yamada et al., Biochemistry, vol. 27, pp. 2193-2196, (1988).
Yamaji et al., Life Sciences, vol. 46, pp. 435-442, (1990).
Natsumeda et al., Biochemical And Biophysical Research Comm., vol. 153, No. 1, pp. 321-327, (1988).
Lui et al., The J. of Biol. Chem., vol. 259, No. 8, pp. 5078-5082, (1984).

(List continued on next page.)

Primary Examiner—John W. Rollins
Assistant Examiner—James O. Wilson
Attorney, Agent, or Firm—Lyon & Lyon

[57] ABSTRACT

The present invention relates to the treatment of neoplastic disease in warm blooded animals using the sequential administration of tiazofurin and ribavirin. Tiazofurin is administered first in a high dose in order to facilitate a sharp decrease in IMP DH activity. These gains are consolidated by the continual administration of tiazofurin until the hematological levels have stabilized and remission is achieved. Once the patient is in remission, ribavirin is administered in steadily tapering dosages until the minimum dosage that will retain the beneficial effect of the tiazofurin is achieved. The IMP DH activity, GTP concentration, and hematological data is continually monitored throughout the treatment and dosages adjusted.

12 Claims, 5 Drawing Sheets

OTHER PUBLICATIONS

Sidwell et al., Antiviral Research, vol. 1, pp. 47–53, (1981).

Natsumeda et al., Biochem and Biophys. Res. Commun., vol. 153, No. 1, pp. 321–327 (1988).

"The Conversion of 2-β-D-Ribofuranosyl-thiazole-4-Carboxamide to an Analogue of NAD With Potent IMP Dehudrogenase-Inhibitory Properties" from *Biochemical Pharmacology* vol. 31, No. 11, pp. 2133–2135, 1982.

"Immunological Control of Virus-associated Tumors in Man: Prospects and Problems" Cancer Research, vol. 36, No. 2 CNREAB-pp. 559–869.

Article from Cancer Research and Clinical Oncology, vol. 98, No. 1, 1980.

*Antiviral Research* vol. 1, No. 1, Mar. 1981 regrding "Bovine Leukemia Virus Inhibition in Vitro by Ribavirin" Proceeding from the seventy-third annual meeting of the American Association for Cancer Reserch, Apr. 28–May 1, 1982.

METHOD FOR THE TREATMENT OF NEOPLASTIC DISEASE UTILIZING TIAZOFURIN AND RIBAVIRIN

BACKGROUND OF INVENTION

A. Field of Invention

This invention is directed to in vivo treatment of neoplastic disease, including leukemia and solid tumors, through the sequential administration of 2-β-D-ribofuranosylthiazole-4-carboxamide and 1-β-D-ribofuranosyl-1,2,4-triazole-3-carboxamide or pharmaceutically acceptable salts thereof.

B. Background Information

Although the arsenal of chemotherapeutic agents for treating neoplastic disease includes a number of clinically useful agents, control of cancer in warm blooded animals still remains a much sought after goal.

Cancer cells are characterized by high levels of inosine monophosphate dehydrogenase (IMP DH) activity. IMP DH is the rate-limiting enzyme of guanosine triphosphate (GTP) biosynthesis and therefore a sensitive target of chemotherapy. Weber, G., *IMP Dehydrogenase and GTP as Targets in Human Leukemia Treatment*, Adv. Exp. Med. Biol. 309B:287–292 (1991). 2-β-D-ribofuranosylthiazole-4-carboxamide (tiazofurin), a synthetic C-nucleoside analogue, has been shown to selectively block IMP DH activity and deplete guanine nucleotide pools, thus forcing the cancer into remission. Weber, G., *Critical Issues in Chemotherapy with Tiazofurin*, Adv. Enzyme Regul. 29:75–95 (1989).

The mechanism behind the tiazofurin inhibition of IMP DH is well known. Tiazofurin is converted to its active metabolite, thiazole-4-carboxamide adenine dinucleotide (TAD), and TAD inhibits the enzyme at the AND-NADH site of IMP DH. Yamada, Y. et al., *IMP Dehydrogenase: Inhibition by the Antileukemic Drug, Tiazofurin*, Leuk. Res. 13(2):179–184 (1989). The affinity of TAD to the enzyme is higher than that of the natural metabolite.

Ribavirin, although primarily utilized as a potent, broad-spectrum antiviral agent, also has been shown to inhibit IMP DH. Yamada, Y. et al., *Action of the Active Metabolites of Tiazofurin and Ribavirin on Purified IMP Dehydrogenase*, Biochem. 27:2193–2196 (1988). It proceeds under a different mechanism than tiazofurin, acting on a different site on the enzyme molecule. It is converted to its active metabolite, ribavirin-monophosphate (RMP), which inhibits the enzyme at the IMP-XMP site of IMP DH. As with tiazofurin, the affinity of its active form to the enzyme is higher than that of the natural metabolite.

Figure 1:
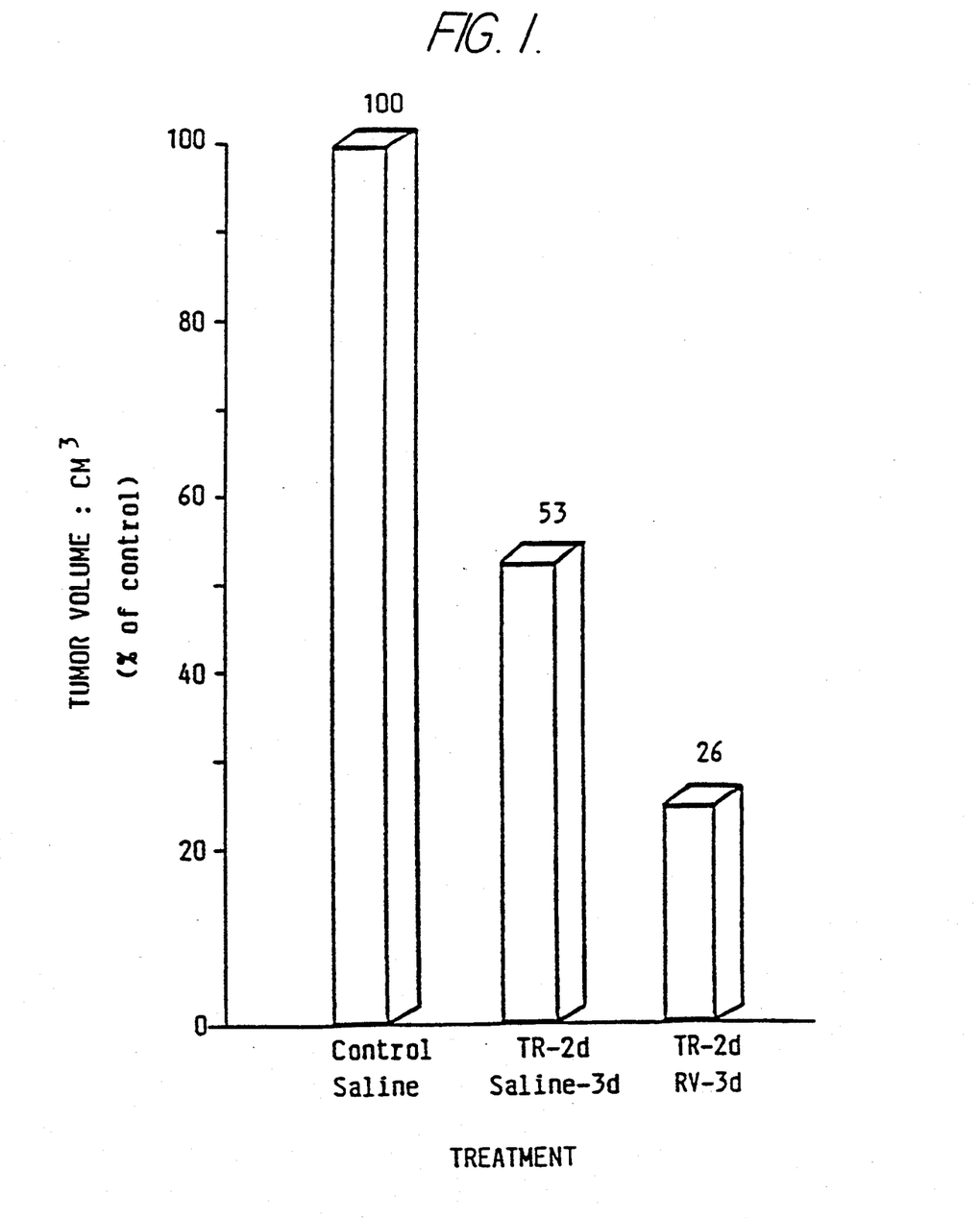
FIG. 1 is a graph of experimental data showing the effect of Tiazofurin and subsequent Ribavirin treatment on IMP DH activity in rat bone marrow.
Figure 2:
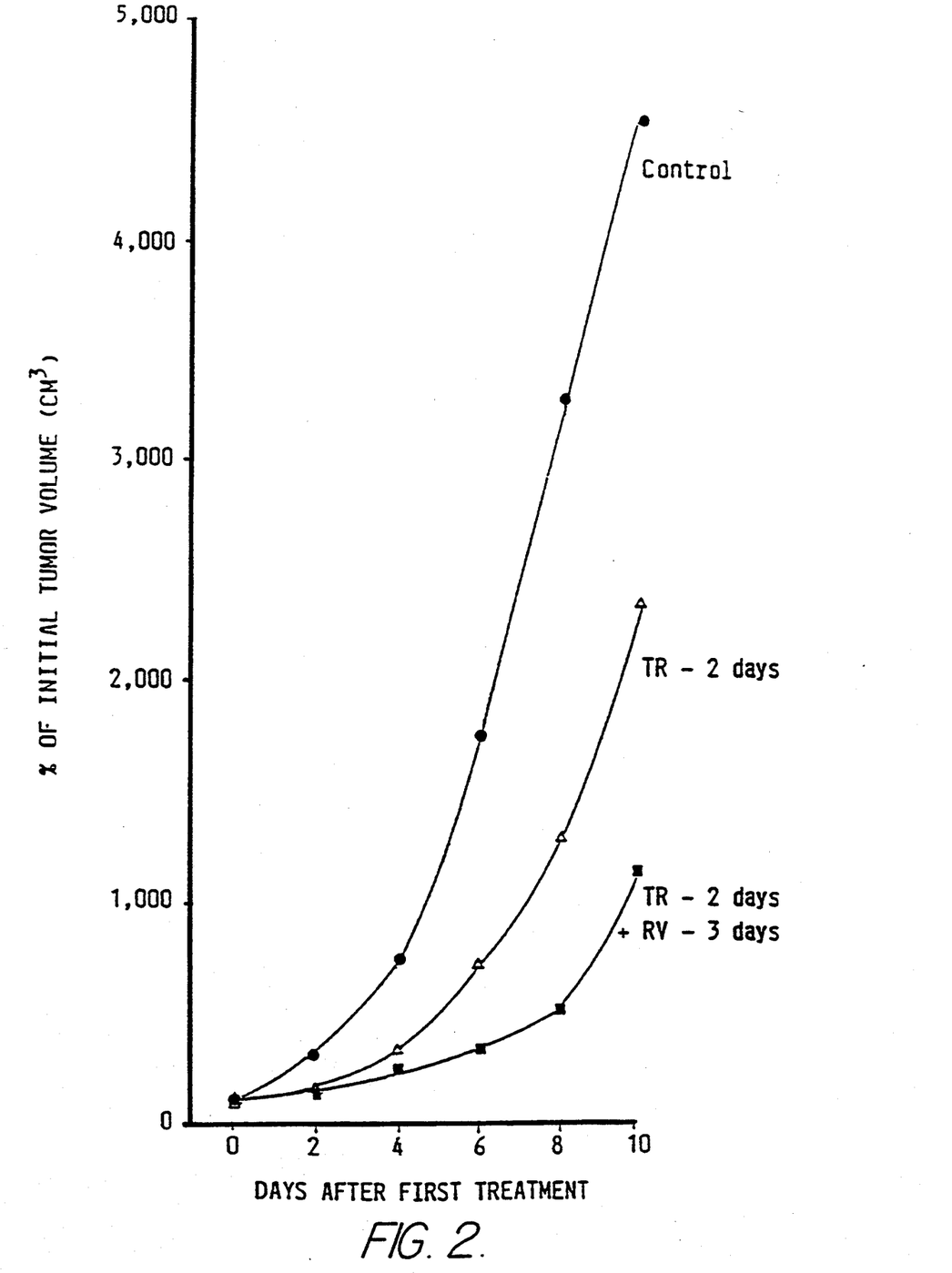
FIG. 2 is a graph of experimental data showing the effect of Tiazofuran and subsequent Ribavirin treatment on cellularity in rat bone marrow.
Figure 3:
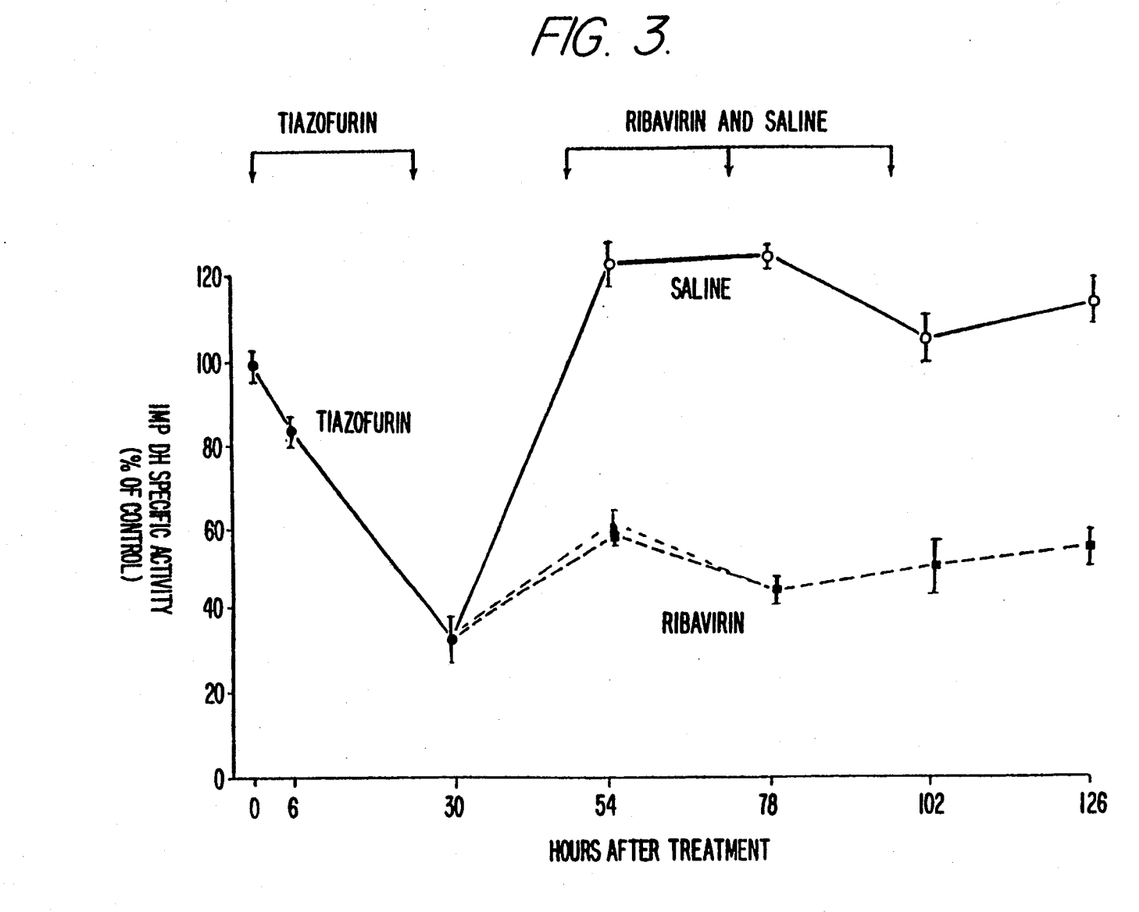
Figure 4:
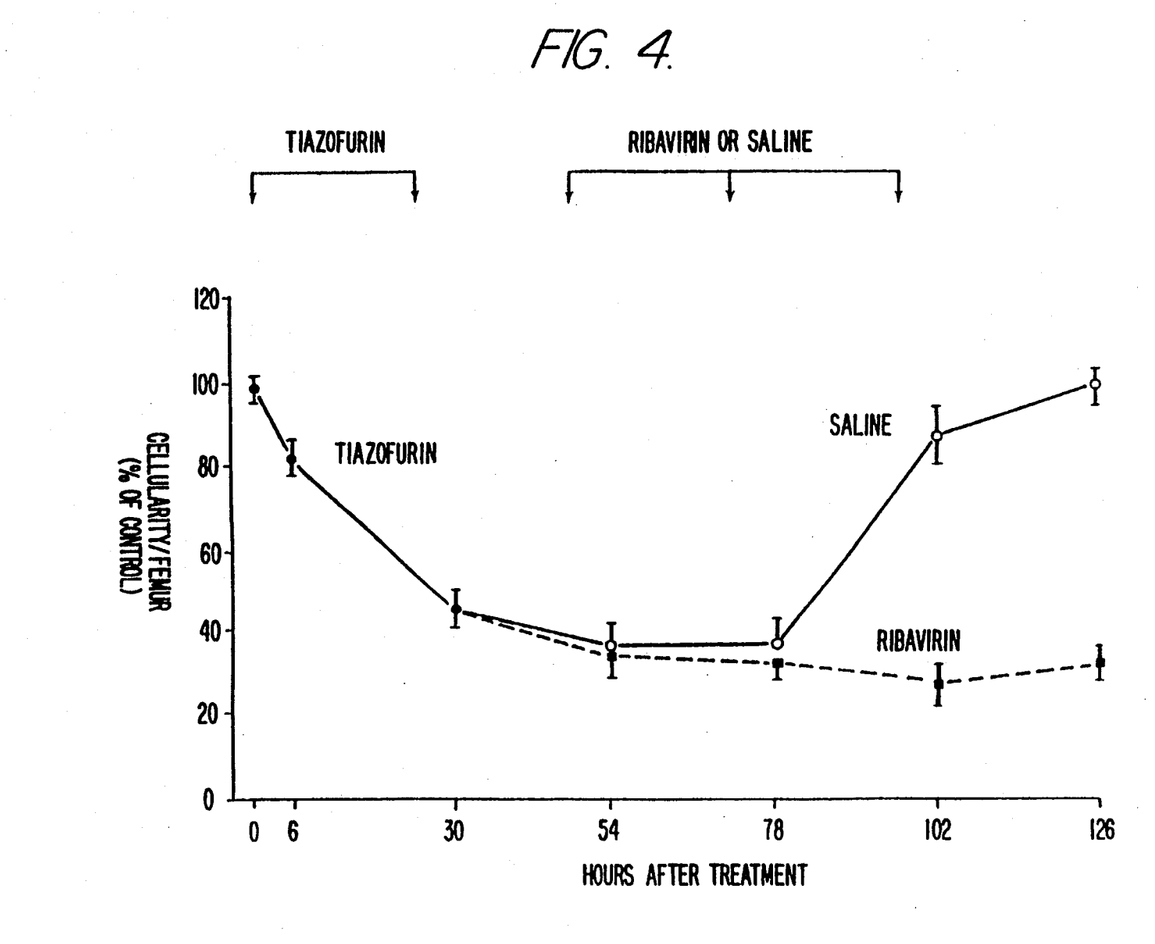
FIG. 4 is a graph of experimental data showing the effect of Tiazofurin and subsequent Ribavirin treatment on tumor growth (H3924a).
Figure 5:
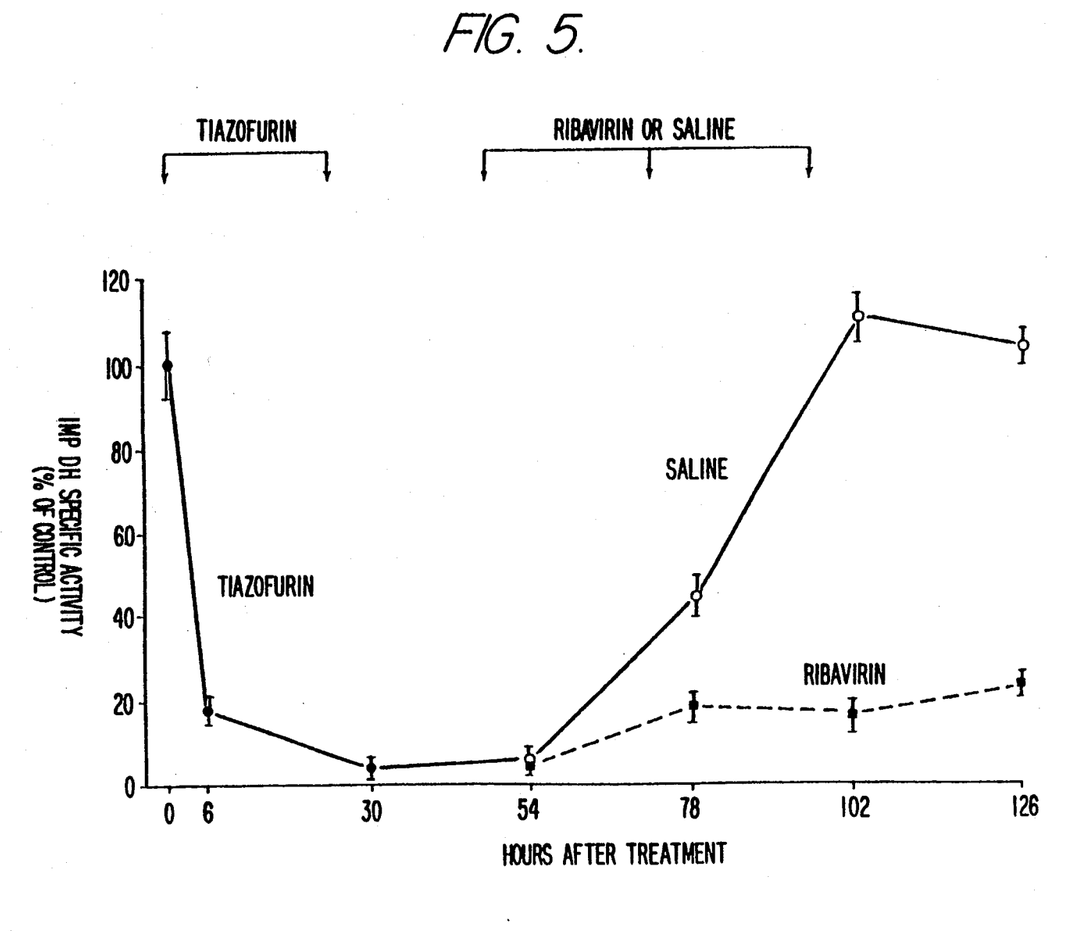
FIG. 5 is a bar chart of experimental data showing the effect of Tiazofurin and subsequent Ribavirin treatment on tumor growth (H3924a).

When ribavirin is administered alone, it is less effective than tiazofurin at lower doses. (see FIGS. 1 and 2). In some cases it has exhibited little or no antitumor effect. Bekesi, J. G. et al., *Treatment of Spontaneous Leukemia in AKR Mice with Chemotherapy, Immunotherapy, or Interferon*, Cancer Research 36:631–639 (1976).

The National Cancer Institute (NCI) defines remission as a patient having a hematology of less than 5% blast cells in the bone marrow. This roughly corresponds with a IMP DH activity of less than 10% activity and a GTP level of less than 20%. Although tiazofurin has been tested in the treatment of cancer patients with positive results, researchers have not yet achieved lasting remission in patients or terminal differentiation of cancerous cells using the compound. Tricot et al., *Tiazofurin: Biological Effects and Clinical Uses*, Int'l J. Cell Clon. 8:161–170 (1990). Within 1 to 3 weeks after infusion with tiazofurin, the remission parameters return to the pre-infusion values. Thus, daily infusions of the compound are necessary.

Daily infusions of tiazofurin can lead to problems of toxic reaction or the development of resistance to the drug. Thus, in order to prolong the remission and keep the patient in the chronic phase, it has been recognized that tiazofurin may have to be administered in conjunction with a second compound. Weber, G., *Critical Issues in Chemotherapy with Tiazofurin*, Adv. Enzyme Reg., 29:75–95 (1989). Researchers have expended a great deal of effort to discover a compound which would have the necessary pharmacological properties to capitalize on the gains achieved by the administration of tiazofurin and to maintain patients in the chronic or remissive state. This process involves extensive research and testing to elucidate effectiveness, toxicity, and proper protocol.

The disclosed invention provides a method of attaining the advantages that have so far eluded researchers. It discloses a method of maintaining the consolidated gains of the tiazofurin-induced remission without the necessity of continual infusion of tiazofurin. As a result, the patient is relieved of the stress and expense of a long term hospital stay and the risks associated with the repeated infusions of tiazofurin. Instead, they can return home and enjoy life.

It provides a unique individualized treatment plan which minimizes side effects by tailoring the dosages to the patient's biochemical needs. Biochemical needs are carefully monitored using GTP concentration, IMP DH activity, and changes in blast cell counts. This allows for accurate fine-tuning of the patient's dose for the maintenance of the patient in the chronic phase with good quality of life.

In view of the inability of current cancer chemotherapeutics to successfully control all neoplastic disease, it is evident that there exists a need for new and additional cancer chemotherapeutic agents and methods of use.

SUMMARY OF INVENTION

The present invention relates to the treatment of neoplastic disease, including leukemia and solid tumors, in warm blooded animals using the sequential administration of tiazofurin and ribavirin. Tiazofurin may be administered first in a high dose in order to induce a sharp decrease in IMP DH activity and GTP concentration. These gains may then be consolidated by the daily infusion of tiazofurin until remission is stabilized. Once the patient is in remission, ribavirin is administered in steadily tapering dosages until the minimum dosage of ribavirin that will retain the beneficial effect of the tiazofurin is reached. The minimum possible dosage is determined by the continual monitoring of IMP DH activity, GTP concentrations, or and hematological data throughout the treatment.

BRIEF DESCRIPTION OF THE DRAWING

FIG. 3 is a graph of experimental data showing the effect of Tiazofurin and subsequent Ribavirin treatment on IMP DH activity in hepatoma 3924a.

DETAILED DESCRIPTION

For the purposes of illustrating this invention, 2-$\beta$-D-ribofuranosylthiazole-4-carboxamide and pharmaceutically acceptable salts thereof will be referred to interchangeably as (a) tiazofurin (nonproprietary name adopted by the United States Adopted Names Council) or (b) under its chemical name above. 1-$\beta$-D-ribofuranosyl-1,2,4-triazole-3-carboxamide and pharmaceutically acceptable salts thereof will be referred to interchangeably as (a) ribavirin (nonproprietary name adopted by the United States Adopted Names Council) or (b) under its chemical name above.

A. Preparation of Tiazofurin and Ribavirin

Tiazofurin may be prepared as described in U.S. Pat. No. 4,680,285 or U.S. Pat. No. 4,451,648, incorporated herein by reference. Ribavirin may be prepared as described in U.S. Pat. No. 4,138,547 or U.S. Pat. No. 3,991,078, incorporated herein by reference. Ribavirin is also commercially available under the trade name Virazole from Viratek, Inc.

B. Modes of Administering Tiazofurin

Tiazofurin may be administered by injection or, preferably, by infusion. Injection may be intravenous, intramuscular, intracerebral, subcutaneous, or intraperitoneal. Infusion may be accomplished through the surgical implantation of a catheter in the patient. The embedded catheter provides a "permanent line" for the administration of tiazofurin. Infusion is preferably carried out over a 60 minute period as described in Jayaram, H. et al., *Clinical Pharmokinetic Study of Tiazofurin Administered as a One Hour Infusion*, Int. J. Cancer 51(2):182–188 (1992), incorporated herein by reference.

For injection or infusion, tiazofurin would be in the form of a solution or suspension. It would be dissolved or suspended in a physiologically compatible solution such that it would be present in a concentration of at least 0.1% by weight of the total composition. Preferably, it would be present in the pharmaceutical carrier at a concentration of about 10% to about 90% by weight of the total composition.

C. Modes of Administering Ribavirin

Ribavirin may be administered by injection or, preferably, orally. Depending on the mode of administration, the compound can be formulated with the appropriate diluents and carriers to form ointments, creams, foams, and solutions having from about 0.01% to about 15% by weight, preferably from about 1% to about 10% by weight of the compound.

For injection, ribavirin is in the form of a solution or suspension, dissolved or suspended in physiologically compatible solution from about 10 mg/ml to about 1500 mg/ml. Injection may be intravenous, intermuscular, intracerebral, subcutaneous, or intraperitoneal.

For oral administration, ribavirin may be in capsule, tablet, oral suspension, or syrup form. The tablet or capsules would contain from about 10 to 500 mg of ribavirin. Preferably they would contain about 300 mg of ribavirin. The capsules will be the usual gelatin capsules and would contain, in addition to the ribavirin in the quantity indicated above, a small quantity, for example less than 5% by weight, magnesium stearate or other excipient. Tablets would contain the foregoing amount of the compound and a binder, which may be a gelatin solution, a starch paste in water, polyvinyl pyrilidone, polyvinyl alcohol in water, etc. with a typical sugar coating.

The syrup would contain from about 50 mg to 200 mg ribavirin per 5 ml of syrup.

D. The Method of Treatment

Treatment is divided into three distinct phases. The "induction phase" refers to the period in which the IMP DH activity of the patient is sharply reduced by a high dose of tiazofurin. The "consolidation phase" refers to the period in which the gains achieved in the induction phase are consolidated, and all the parameters of remission are fully accomplished. The "maintenance phase" refers to the period in which the patient is maintained in remission. "Remission" is defined by an IMP DH level less than 10%, a GTP level less than 20%, or hematology of less than 5% blast cells in the bone marrow.

The induction phase is characterized by an initial high dose of tiazofurin, designed to sharply reduce IMP DH activity. This would be accomplished by administering more than 4,400 mg/m$^2$ of the compound. Preferably, the dose would be 4,400 mg/m$^2$.

This high dose of tiazofurin is administered until the IMP DH activity is decreased into the range of 0 to 10%. Preferably, in the range of 0 to 5%. IMP DH activity is preferably monitored using the methods described in Ikegami, T. et al., *Direct Assay Method for Inosine 5'-monophosphate Dehydrogenase Activity*, Anal. Biochem. 150:155–160 (1985). Although the dose and time period may vary, the preferred range would be achieved in approximately 2 days when daily doses of 4,400 mg/m$^2$ are administered.

When the desired IMP DH activity is achieved, the treatment enters the consolidation phase. This phase is characterized by lower doses of tiazofurin administered until the patient has stabilized in remission. Although the time period may vary, this would be achieved within 5 to 12 days.

Effective amounts of tiazofurin in the consolidation phase, would typically range from 1100 to 3300 mg/m$^2$. Preferably, the dose would be about 2200 mg/m$^2$. In any event, the actual amount should be sufficient to provide an effective amount of the agent to consolidate the gains of the induction phase, as indicated by the hematological and IMP DH activity data, all of which will be readily within the ability of those skilled in the art to determine given the disclosure herein.

After the consolidation phase, the treatment enters into its third and final stage, the maintenance phase. The maintenance phase, is strategically designed to keep the patient in remission using ribavirin. Ribavirin would be initially administered at a high dose, typically in the range of 1,100 to 3,300 mg/m$^2$. Preferably, the dose should be about 2,200 mg/m$^2$. This dose would then be gradually tapered until the afflicted animal is consuming the lowest possible dose to maintain remission. Typically, the dose will be fine-tuned in 100 mg increments.

Dosage success would be tracked by careful use of an IMP DH activity assay, GTP concentration, or blast cell counts. Although the dose will clearly vary depending on the individual circumstance, the lowest dose necessary for remission will typically be achieved at around 900 mg/m$^2$. In any event, the actual amount should be sufficient to maintain IMP DH in the range of 1 to 20%. Preferably, maintaining IMP DH activity in the range of 1 to 10% or the blast cell counts less than 5%. This will be readily within the ability of those skilled in the art given the disclosure herein.

EXAMPLE 1

In this example, ACI/N rats bearing s.c. transplanted hepatoma 3924A were administered daily i.p. injections of 150 mg/kg tiazofurin (trade name Tiazole, Viratek, Inc.) for two days. The rats were then divided into two groups: one received daily i.p. injections of saline, the other received 100 mg/kg ribavirin (trade name Virazole, Viratek, Inc.) for an additional two days.

Tiazofurin reduced the IMP DH activity to 10% and ribavirin maintained the inhibition of IMP DH activity at 20–30% of the control values. The IMP DH activity in the saline-treated rats returned to the untreated levels. (see FIGS. 1 through 5).

EXAMPLE 2

Patients with chronic granulocytic leukemia in blast crisis would be treated with two daily infusions of 4,400 mg/m$^2$ of tiazofurin (trade name tiazole, Viratek, Inc.) for two days, followed by 12–13 days of a daily 2,200 mg/m$^2$ dose of tiazofurin. This treatment would be followed by a daily declining dose of ribavirin (trade name Virazole, Viratek, Inc.), beginning at 2,200 mg/m$^2$ and dropping to 900 mg/m$^2$. In order to control uric acid levels, allopurinol will be administered in 6 to 8 doses, totalling 800 mg, over 24 hours. This should also serve to increase hypoxanthine in the plasma. The constant monitoring by IMP DH assays in the blast cells will allow the administrator to reduce the ribavirin dose and yet maintain the patients in remission.

EXAMPLE 3

Patients with ovarian cancer would be treated with two daily infusions of 4,400 mg/m$^2$ of tiazofurin (trade name tiazole, Viratek, Inc.) for two days, followed by 12–13 days of a daily 2,200 mg/m$^2$ dose of tiazofurin. This treatment would be followed by a daily declining dose of ribavirin (trade name Virazole, Viratek, Inc.), beginning at 2,200 mg/m$^2$ and dropping to 900 mg/m$^2$. In order to control uric acid levels, allopurinol will be administered in 6 to 8 doses, totalling 800 mg, over 24 hours. This should also serve to increase hypoxanthine in the plasma. The constant monitoring by IMP DH assays and GTP concentration will allow the administrator to reduce the ribavirin dose and yet maintain the patients in remission.

It is to be understood that the above-described embodiments are illustrative only and that modifications thereof may occur to those skilled in the art. Accordingly, this invention is not to be regarded as limited to the embodiments disclosed herein, but is to be limited only as defined by the appended claims.

I claim:

1. A method of treating neoplastic disease in warm blooded animals, wherein the neoplastic tissue is characterized by elevated IMP DH activity, comprising:
   administering a therapeutically effective dose of a first pharmaceutical composition containing as its active component 2-β-D-ribofuranoxylthiazole-4-carboxamide or pharmaceutically acceptable salts thereof to reduce the IMP DH activity of cancer cells to the range of 1 to 10%; and
   following the first pharmaceutical composition with the administration of a second pharmaceutical composition containing as its active component 1-β-D-ribofuranosyl-1,2,4-triazole-3-carboxamide or pharmaceutically acceptable salts thereof to maintain a physiological characteristic in the animal selected from at least one of IMP DH level less than 10%, a GTP level less than 20%, and hematology of less than 5% blast cells in the bone marrow.

2. A method of treating neoplastic disease in warm blooded animals, wherein the neoplastic tissue is characterized by elevated IMP DH activity, comprising:
   administering a high induction dose of a first pharmaceutical composition containing as its active component 2-β-ribofuranosylthiazole-4-carboxamide or pharmaceutically acceptable salts thereof to reduce the IMP DH activity of cancer cells to the range of 1 to 10%;
   following the administration of the high induction dose with the administration of a lower consolidation dose of the first pharmaceutical composition; and
   following the administration of the lower consolidation does with the administration of a second pharmaceutical composition containing as its active component 1-β-D-ribofuranosyl-1,2,3-triazole-3-carboxamide or pharmaceutically acceptable salts thereof to maintain a physiological characteristic in the animal selected from at least one of the IMP BH level less than 10%, a GTP level less than 20%, and hematology of less than 5% blast cells in the bone marrow.

3. A method of treating neoplastic disease in warm blooded animals as in claim 2 wherein:
   the high induction dose is administered until IMP DH activity drops to the range of 0 to 5%

4. A method of treating neoplastic disease in warm blooded animals, as in claim 2, wherein:
   the high induction dose comprises more than 4400 mg/m$^2$ of the first pharmaceutical composition.

5. A method of treating neoplastic disease in warm blooded animals, as in claims 2 or 4 wherein:
   the lower consolidation dose comprises 1100 to 3300 mg/m$^2$ of the said first pharmaceutical composition.

6. A method of treating neoplastic disease in warm blooded animals, as in claim 5 wherein:
   the lower consolidation dose comprises 2200 mg/m$^2$ of the said first pharmaceutical composition.

7. A method of treating neoplastic disease in warm blooded animals, as in claim 2, wherein:
   the second pharmaceutical compound is adjusted to maintain IMP DH activity at 1 to 10%.

8. A method of treating neoplastic disease in warm blooded animals, as in claim 7, wherein:
   the second pharmaceutical compound is adjusted to maintain IMP DH activity at 1 to 5%.

9. A method of treating neoplastic disease in warm blooded animals, wherein the neoplastic tissue is characterized by elevated IMP DH activity, comprising:
   administering a 3,500 to 4,800 mg/m$^2$ high dose of a first pharmaceutical composition containing as its active component 2-β-D-ribofuranosylthiazole-4-carboxamide or pharmaceutically acceptable salts thereof daily for 2 days to reduce the IMP DH activity of cancer cells to the range of 1 to 10%;

followed by a 1,800 to 2,600 mg/m² consolidation dose of the first pharmaceutical composition administered daily for 10–15 days;

followed by a 1,800 to 2,600 mg/m² maintenance dose of a second pharmaceutical composition containing as its active compnent 1-β-D-ribofuranosyl-1,2,4-triazole-3-carboxamide or pharmaceutically acceptable salts thereof, gradually tapering to 900 mg/m², to maintain a physiological characteristic in the animal selected from at least one of IMP BH level less than 10%, a GTP level less than 20%, and hematology of less than 5% blast cells in the bone marrow.

10. A method of treating neoplastic disease in warm blooded animals, as in claim 9, wherein:

the high dose is in the range of 3800 to 4600 mg/m²;

the consolidation dose is in the range of 2000 to 2400 mg/m²; and the maintenance dose is started in the range of 2000 to 2400 mg/m².

11. A method of treating neoplastic disease in warm blooded animals, as in claim 10, wherein:

the high dose is in the range of 4300 to 4500 mg/m²;

the consolidation dose is in the range of 2100 to 2300 mg/m²; and the maintenance dose is started in the range of 2100 to 2300 mg/m².

12. A method of treating neoplastic disease in warm blooded animals, as in claims 1, 2 or 9, wherein:

the first and second pharmaceutical compositions are administered by at least one of injection, infusion and by mouth.

* * * * *